United States Patent
Glenn

(10) Patent No.: US 8,066,008 B2
(45) Date of Patent: Nov. 29, 2011

(54) CONDOM WITH ANTI-RUPTURE MEANS AND SECURING MEANS

(76) Inventor: Andre Glenn, Decatur, GA (US)

(*) Notice: Subject to any disclaimer, the term of this patent is extended or adjusted under 35 U.S.C. 154(b) by 72 days.

(21) Appl. No.: 12/068,597

(22) Filed: Feb. 8, 2008

(65) Prior Publication Data

US 2009/0199859 A1 Aug. 13, 2009

(51) Int. Cl.
*A61F 6/02* (2006.01)
*A61F 5/44* (2006.01)

(52) U.S. Cl. ........ 128/844; 128/842; 128/914; 128/918; 604/349; 602/902

(58) Field of Classification Search .......... 128/830, 128/832, 834, 844, 842, 917, 918; 604/349; 602/902; 600/38–41
See application file for complete search history.

(56) References Cited

U.S. PATENT DOCUMENTS

| | | | | |
|---|---|---|---|---|
| 2,586,674 A | * | 2/1952 | Lonne | 128/844 |
| 4,354,494 A | | 10/1982 | Hogin | |
| 4,735,621 A | | 4/1988 | Hessel | |
| 4,834,114 A | | 5/1989 | Boarman | |
| 4,972,849 A | * | 11/1990 | Park et al. | 128/842 |
| 5,121,755 A | | 6/1992 | Hegedusch | |
| 5,370,130 A | * | 12/1994 | Hess | 128/844 |
| 5,370,131 A | * | 12/1994 | Hess | 128/844 |
| 5,666,971 A | | 9/1997 | Anatolievich | |
| 5,799,657 A | * | 9/1998 | Pasczuk et al. | 128/844 |
| 5,979,448 A | | 11/1999 | Weller et al. | |
| 6,102,043 A | | 8/2000 | Johnson | |
| 6,123,079 A | | 9/2000 | Johnson | |
| D434,138 S | * | 11/2000 | DeVries | D24/105 |
| 6,182,661 B1 | * | 2/2001 | Solanki et al. | 128/844 |
| 6,213,123 B1 | * | 4/2001 | Miller et al. | 128/842 |
| 6,453,903 B1 | | 9/2002 | Thomas, III | |
| 6,478,027 B1 | | 11/2002 | Serrano et al. | |
| 7,131,443 B2 | | 11/2006 | Van Gaalen | |
| D603,039 S | * | 10/2009 | Resnic | D24/105 |

* cited by examiner

*Primary Examiner* — Michael Brown
*Assistant Examiner* — Brandon Jackson
(74) *Attorney, Agent, or Firm* — Malik N. Drake

(57) ABSTRACT

A prophylactic device providing the wearer with increased protection against slippage and ruptures. The device has a tubular body with an extra strength tip and a band. The band is elastic and has a ring that stretches to pass comfortably over a wearer's testicles. The band secures the prophylactic device to the wearer and prevents the device from slipping off of the wearer. Both the extra strength tip and the band are thicker than the tubular body and provide the wearer protection against ruptures.

10 Claims, 2 Drawing Sheets

CONDOM WITH ANTI-RUPTURE MEANS AND SECURING MEANS

FIELD OF THE INVENTION

This invention relates generally to contraceptive and prophylactic devices.

BACKGROUND OF THE INVENTION

A conventional condom comprises an elongate thin tubular sheath made of a resilient material. The sheath is closed on one end and open at the other end to provide for insertion of a penis. The condom is typically rolled into a relatively thin disc during manufacture thereof to provide for compact storage and to provide for ease of application of the condom. Conventional condoms are considered to be very effective in preventing unwanted pregnancies and transmission of venereal diseases. However, during coitus, a conventional condom is susceptible to slipping off. This slippage has the obvious disadvantage of potentially allowing leakage of semen or other bodily fluids. Further, a conventional condom, which tends to function best when the penis is fully erect, may slip with regards to a partially erect penis. This is particularly significant after ejaculation if the penis remains in the vagina. In that case, the penis may soften, and become smaller, thus allowing for possible slippage (i.e., the condom may slip off of the wearer).

A conventional condom is also susceptible to breaks or ruptures. Again, such occurrences have the obvious disadvantage of potentially allowing leakage of semen or other bodily fluids.

A search of the prior art shows that there a numerous patents relating to condoms. All of these patents disclose condoms constructed of conventional materials and thickness. Therefore, none provide the wearer protection against breaks or ruptures. Some of these patents disclose a condom equipped with retaining apparatus to secure the condom to the user. However, the retaining devices disclosed are straps that must be tied together or are otherwise discontinuous. These methods of keeping the condom attached to the wearer allow for the condom to become untied or otherwise unsecured and, thus, may allow for slippage. Consequently, there is a need for a condom that fits comfortably on the wearer and that will not break or accidentally slip off. A search of the prior art shows that no such condom is known.

SUMMARY OF THE INVENTION

It is a primary objective of the present invention to provide a prophylactic device that can be used by a male wearer to help prevent pregnancy or transmission of sexually transmitted diseases. More particularly, it is an objective of the present invention to provide a prophylactic device that attaches to a wearer and is sufficiently secured so that the contraceptive device will not slip off.

It is another objective of the present invention to provide a prophylactic device that protects the wearer against breaks and ruptures of the prophylactic device.

It is still another objective of the present invention to provide a prophylactic device that promotes fuller, thicker erections achieved by the male wearer.

It is a further objective of the present invention to provide a prophylactic device that gives the male wearer the guaranty that the condom is positioned correctly on the wearer's penis.

The prophylactic device is comprised of a condom (which comprises a tip and a longitudinal body), and a band. The tip and band of the condom are thicker than the body (which is of conventional thickness), thereby providing the wearer assurances that the tip and band will not break or rupture. The band is durable, stretchable, and fits comfortably over the wearer's penis and testicles. The correct positioning of the band around the wearer's testicles helps to promote longer, fuller erections. Just beyond the extra safety tip, the condom has three dots that protrude from the condom. When positioned properly on the wearer, these three dots will be on the topside of the condom (i.e., the wearer would be able to look directly down at the condom and see the dots). This feature helps to ensure that the condom is positioned properly on the wearer. The condom may also have ribs along the longitudinal body, thereby providing a more intense sensation for the wearer's sexual partner.

BRIEF DESCRIPTION OF THE DRAWINGS

Preferred and alternative embodiments of the present invention are described in detail below with reference to the following drawings.

DETAILED DESCRIPTION OF THE PREFERRED EMBODIMENT

Figure 1:
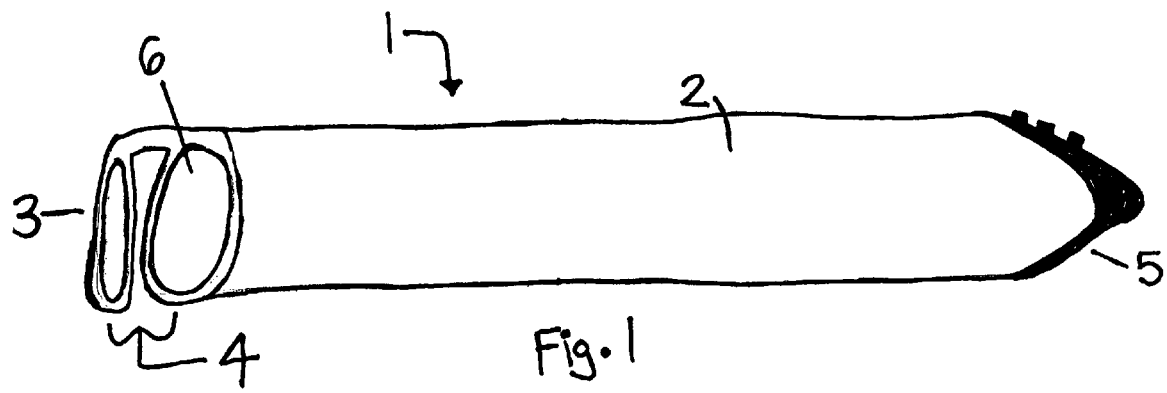
FIG. 1 is a side view of the fully unrolled (unoccupied) condom, in accordance with an embodiment of the present invention.

Referring to FIG. 1, a prophylactic device 1 is comprised of a condom 2 a band 3, and a gap 4. In a first preferred embodiment, the prophylactic device 1 is constructed of latex. The condom has an extra safety tip 5 and a condom opening 6. Both the extra safety tip 5 and the band 3 are thicker than the rest of the prophylactic device 1. The added thickness helps to prevent breaks and/or ruptures in the prophylactic device 1.

Figure 2:
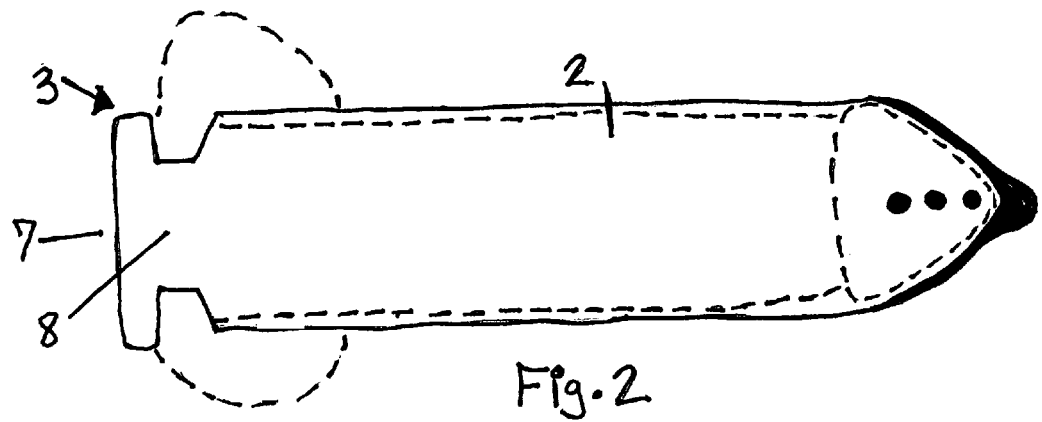
FIG. 2 is a top view of the prophylactic device, fully unrolled and secured onto a wearer.

Referring to FIG. 2, the band 3 is attached to the condom 2 at the top of the condom opening 6. The band 3 is continuous and is comprised of a continuous band ring 7 and a continuous connector 8 that joins the band ring 7 to the condom 2. The connector 8 provides a continuous connection from the condom 2 to the band ring 7. Since the band 3, which securely attaches to the wearer preventing the condom from inadvertently slipping off, is continuous and does not have straps, claps, or other similar attachment means, the wearer does not have to worry about the condom becoming unattached (from the wearer).

Figure 3:
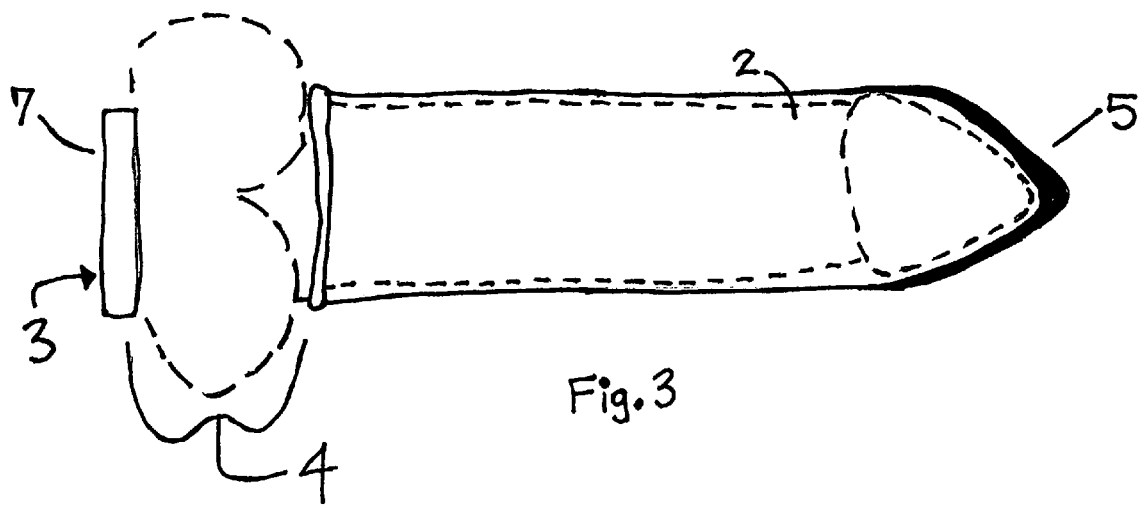
FIG. 3 is a bottom view of the prophylactic device of FIG. 2.

As is shown in FIG. 3, the gap 4 allows for the band 3 to fit comfortably around the wearer's testicles.

Figure 4:
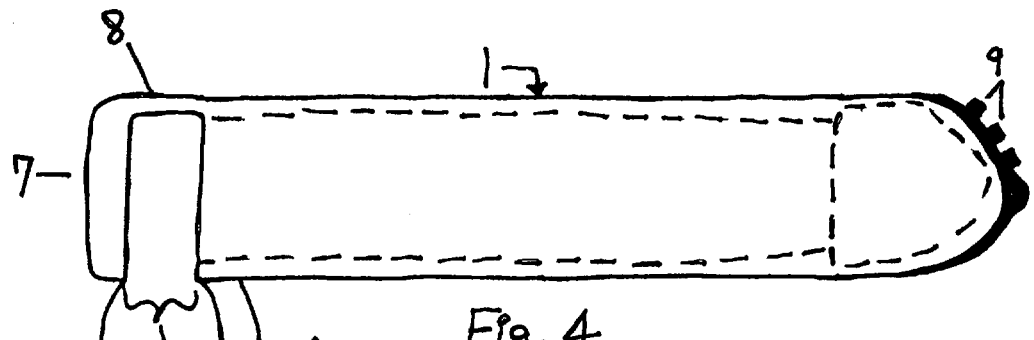
FIG. 4 is a side view of the prophylactic device of FIG. 1, as the device is worn by a wearer.

Referring to FIG. 4, when the wearer has properly put on the prophylactic device 1, the dots 9 and connector 8 are on top and the gap 4 is under the connector 8, thereby accommodating the wearer's testicles.

Figure 5:
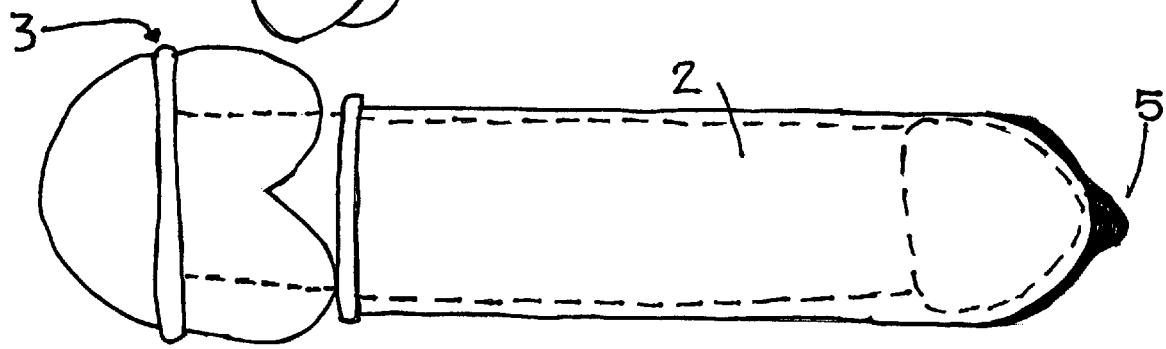
FIG. 5 is a bottom view of the prophylactic device, wherein the condom is not yet fully secured unto the wearer and the band is being stretched to fit around the wearer's testicles.

Referring to FIG. 5, it can be seen that the band 3 is sufficiently elastic so that it can be stretched to pass over the wearer's testicles.

Figure 6:
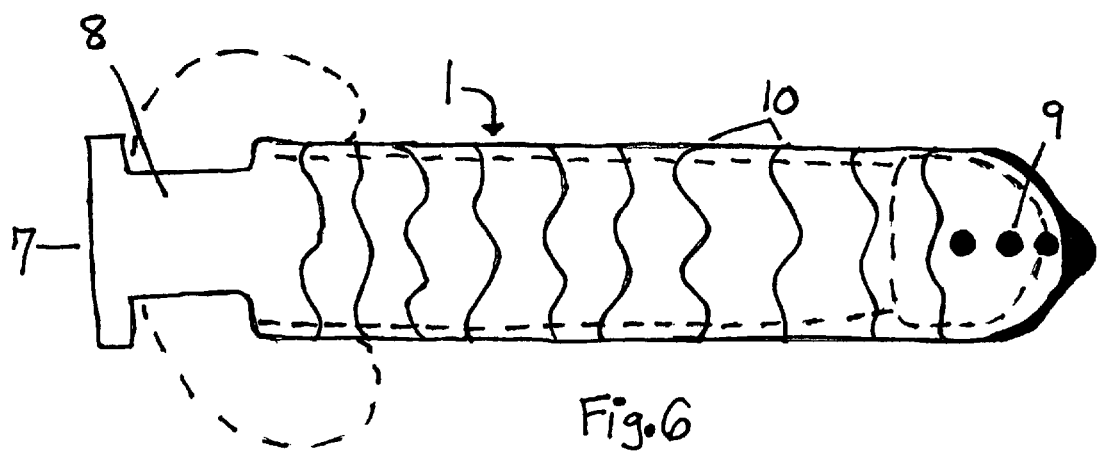
FIG. 6 is a top view of the prophylactic device having ribs, in accordance with an alternative embodiment of the invention.

Referring to FIG. 6, an alternative embodiment is shown. The prophylactic device 1 also comprises a plurality of circular ribs 10, spaced apart along the length of the condom. The plurality of ribs may be positioned along a portion of the condom or along the entire length of the condom. In addition to being circular, the ribs are also wavy-shaped. The ribs provide added pleasure for the wearer's sexual partner.

While the preferred embodiment of the invention has been described, various alternative embodiments of the invention are possible without departing from the spirit and scope of the invention. For example, the prophylactic device may be constructed of any elastic material. Also, although the preferred embodiment discloses three dots, the prophylactic device may have any number of dots. Accordingly, the scope of the invention is not limited by the disclosure of the preferred embodiment.

What is claimed is:

1. A prophylactic device comprising:
   a tubular body defining a longitudinal axis and having a thin wall, a closed distal end, and an open proximal end;
   a continuous band extending from the open proximal end; and
   no more than one line of 3 dots;
   wherein the no more than one line of 3 dots comprises a plurality of dots positioned longitudinally, and is proximately located in relation to the closed distal end.

2. The prophylactic device of claim 1, wherein the continuous band comprises a continuous connector and a continuous band ring.

3. The prophylactic device of claim 2, wherein the continuous band is thicker than the tubular body.

4. The prophylactic device of claim 3, further comprising an extra safety tip that is located at the closed distal end and is constructed of the same material as the tubular body.

5. The prophylactic device of claim 4, wherein the extra safety tip is thicker than the tubular body.

6. The prophylactic device of claim 5, wherein the continuous connector joins the tubular body and the continuous band ring.

7. The prophylactic device of claim 6, wherein the prophylactic device is constructed of an elastic material.

8. The prophylactic device of claim 7, further comprising a plurality of ribs.

9. The prophylactic device of claim 8, wherein each rib of the plurality of ribs is circular (thereby going around the circumference of the tubular body), has at least one nearest adjacent rib, is spaced apart from the at least one nearest adjacent rib, and is wavy-shaped.

10. The prophylactic device of claim 9, wherein the plurality of ribs is positioned along the entire length of the tubular body.

\* \* \* \* \*